(12) United States Patent
Nishiyama

(10) Patent No.: US 7,745,785 B2
(45) Date of Patent: Jun. 29, 2010

(54) SAMPLE INSPECTION METHOD, SAMPLE INSPECTION APPARATUS, AND SAMPLE HOLDER

(75) Inventor: Hidetoshi Nishiyama, Tokyo (JP)

(73) Assignee: JEOL Ltd., Tokyo (JP)

( * ) Notice: Subject to any disclaimer, the term of this patent is extended or adjusted under 35 U.S.C. 154(b) by 353 days.

(21) Appl. No.: 11/951,429

(22) Filed: Dec. 6, 2007

(65) Prior Publication Data

US 2008/0135751 A1    Jun. 12, 2008

(30) Foreign Application Priority Data

Dec. 6, 2006  (JP) ............................. 2006-328959

(51) Int. Cl.
*G01N 23/00*    (2006.01)
(52) U.S. Cl. ...................... 250/311; 250/306; 250/307; 250/310; 250/492.3
(58) Field of Classification Search ................. 250/305, 250/306, 307, 310, 311, 492.3
See application file for complete search history.

(56) References Cited

FOREIGN PATENT DOCUMENTS

JP   06-318445    11/1994
JP   2004-515049   5/2004

OTHER PUBLICATIONS

Green, Evan Drake Harrima, Ph.D., Atmospheric Scanning Electron Microscope, Chapter I, Introduction, Stanford University, 1993, pp. 1-12.

*Primary Examiner*—Jack I Berman
*Assistant Examiner*—Hanway Chang
(74) *Attorney, Agent, or Firm*—The Webb Law Firm

(57) ABSTRACT

A sample holder is offered which is used when a sample is inspected by irradiating the sample with a primary beam consisting of a charged-particle beam (such as an electron beam) via a film. Furthermore, method and apparatus for preventing destruction of the film due to a pressure difference by detecting damage to the film during inspection are offered.

18 Claims, 6 Drawing Sheets

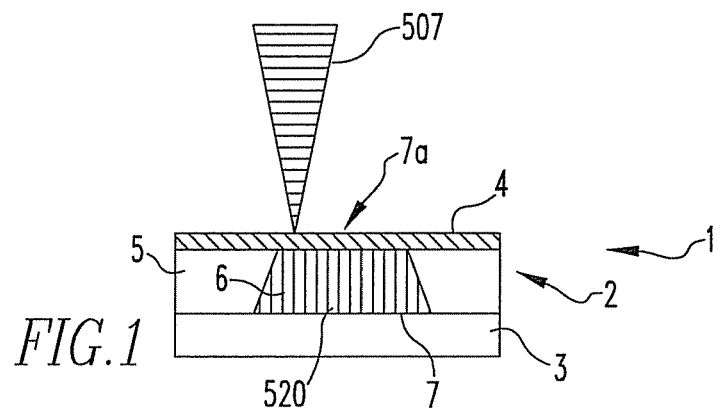
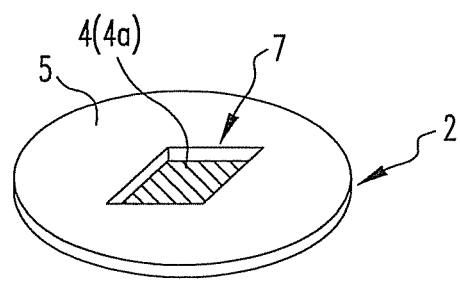
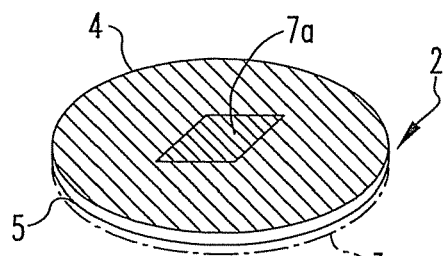
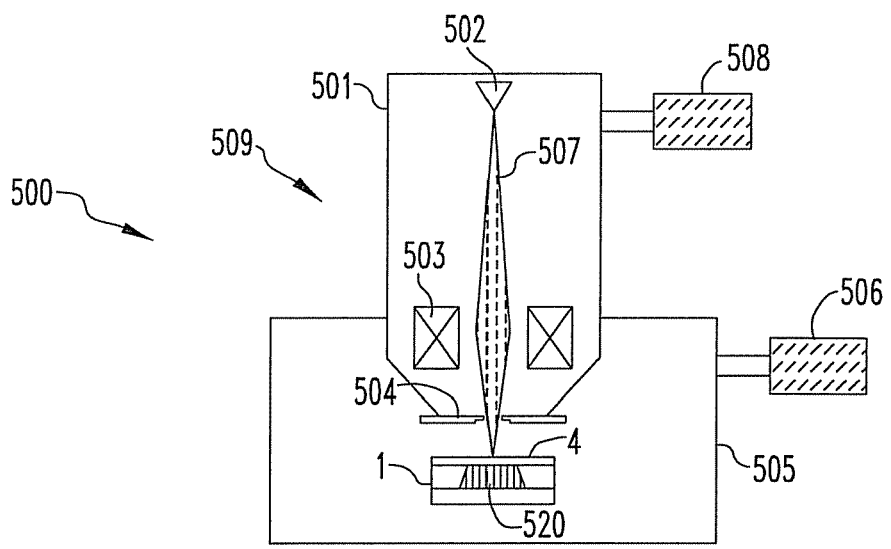

SAMPLE INSPECTION METHOD, SAMPLE INSPECTION APPARATUS, AND SAMPLE HOLDER

BACKGROUND OF THE INVENTION

1. Field of the Invention

The present invention relates to a method of inspecting a sample by irradiating it with a primary beam, such as a charged-particle beam, via a film and detecting a secondary signal emanating from the sample in response to the irradiation. Furthermore, the present invention relates to a sample inspection apparatus adapted for use in this method. The present invention also relates to a sample holder adapted to be used in this method.

2. Description of Related Art

In a sample inspection apparatus incorporating the facilities of a scanning electron microscope (SEM), a sample to be investigated is normally placed within a sample chamber whose inside has been evacuated by means of pumping. The sample placed in the sample chamber that is in the reduced pressure ambient is irradiated with a primary beam, such as a charged-particle beam (e.g., an electron beam). As a result, various secondary signals, such as backscattered electrons, secondary electrons, fluorescence, and X-rays, are produced from the sample. Any kind of the secondary signals is detected, and an image of the sample is created based on the detected signal. Thus, the sample is inspected.

Accordingly, when the sample under inspection contains moisture, it is necessary to prevent evaporation of the moisture from the sample. Consequently, it is necessary to prevent the sample from being exposed to the reduced pressure ambient within the sample chamber.

One conceivable method of inspecting a sample by SEM without exposing the sample to such a reduced pressure ambient consists of preparing a sample holder having an aperture that has been closed off by a film, placing the sample in the holder, and placing the holder within the SEM sample chamber that is in a reduced pressure ambient.

The inside of the sample holder in which a sample is placed is not evacuated. The film that covers the opening formed in the sample holder can withstand the pressure difference between the reduced pressure ambient in the SEM sample chamber and the non-evacuated ambient (e.g., atmospheric-pressure ambient) inside the sample holder. Also, the film permits transmission of an electron beam (see, for example, JP-T-2004-515049).

When a sample is inspected, an electron beam is directed from outside the sample holder at the sample placed in the holder via the film on the sample holder disposed in the SEM sample chamber that is in a reduced-pressure ambient. Backscattered electrons are emitted from the irradiated sample. The electrons penetrate through the film on the sample holder and are detected by a detector mounted in the SEM sample chamber. As a result, an SEM image of the sample is obtained.

Another example in which a sample is irradiated with an electron beam via a film withstanding the pressure difference between vacuum and atmospheric pressure and an SEM image is derived by detecting backscattered electrons emitted from the sample is described in Atmospheric scanning electron microscopy, Green, Evan Drake Harriman, Ph. D., Stanford University, 1993 (especially, Chapter 1: Introduction).

It is also possible to form a pair of opposite films from the above-described film. A sample is placed between the films, and a TEM (transmission electron microscope) image can be obtained. This technique is described in JP-A-47-24961 and JP-A-6-318445. Especially, in JP-A-47-24961, a case where an SEM image of the sample placed between such a pair of films is obtained is described.

In the above-described specimen inspection procedure, a primary beam, such as an electron beam, is directed at the sample via a film. A secondary signal, such as backscattered electrons, emitted from the sample in response to the irradiation is detected, and the sample is inspected.

In this inspection procedure, it is necessary to prepare a different sample holder for each kind of sample. Therefore, the sample holders used in this sample inspection are preferably inexpensive.

SUMMARY OF THE INVENTION

Accordingly, it is an object of the present invention to provide an inexpensive sample holder which is used when a sample is inspected by directing a primary beam consisting of a charged-particle beam (such as an electron beam) at the sample via a film as described previously and which is simple in structure.

The primary beam irradiation of the film produces damage to the film. That is, when the electron beam enters the film, coupling between molecules forming the film is gradually destroyed. This deteriorates the resistance of the film to the pressure difference between vacuum and atmospheric pressure.

Especially, the film is very thin because it permits the electron beam to pass through the film. If the strength of the film deteriorates due to beam irradiation damage, the film may no longer withstand the pressure difference.

Where the film damaged as described above is destroyed by the pressure difference, the liquid component of the sample (containing moisture) held on the film leaks into the sample chamber. This will contaminate the inside of the SEM instrument. Especially, if the sample contains components harmful to the human body, it is essential to prevent contamination of the instrument due to film destruction.

In view of the foregoing problem, it is another object of the present invention to provide a method of inspecting a sample in such a way that when the sample is irradiated with a primary beam, such as an electron beam, via a film for the inspection, damage to the film due to beam irradiation is detected and thus destruction of the film due to a pressure difference can be prevented. It is a further object of the present invention to provide a sample inspection apparatus adapted to implement this method.

A sample inspection method according to a first embodiment of the present invention is used to inspect a sample by irradiating the sample with a primary beam via a film and detecting a secondary signal emitted from the sample in response to the beam irradiation. In this method, information about the film obtained in response to the irradiation is monitored, and/or a dose of the primary beam impinging on the film is monitored.

A sample inspection apparatus according to another embodiment of the present invention has: a film having a first surface on which a sample is held; a vacuum chamber for reducing the pressure of an ambient in contact with a second surface of the film; irradiation apparatus connected with the vacuum chamber and irradiating the sample with a primary beam via the film; and signal detection apparatus for detecting a secondary signal emitted from the sample in response to the beam irradiation. The inspection apparatus includes: monitoring device for monitoring information about the film obtained in response to the irradiation and/or monitoring device for monitoring a dose of the primary beam impinging on the film.

A second sample inspection apparatus according to another embodiment of the present invention has: two films disposed opposite to each other such that a sample is held between mutually opposite surfaces of the films; a vacuum chamber for reducing the pressure of an ambient in contact with surfaces of the films facing away from the mutually opposite surfaces; irradiation apparatus connected with the vacuum chamber and irradiating the sample with a primary beam via one of the films; and signal detection apparatus for detecting a secondary signal produced from the sample in response to the beam irradiation. The sample inspection apparatus includes: a monitoring device for monitoring information about the film obtained in response to the irradiation and/or a monitoring device for monitoring a dose of the primary beam impinging on the film.

A sample holder according to another embodiment of the present invention has a film through which a beam of charged particles is transmitted. The film has a first and a second surface. A sample that is placed on the first surface of the film can be irradiated with the beam of charged particles from a side of the second surface of the film via the film. In this sample holder, a fixing member is mounted on the first surface of the film except for a sample-holding region. The sample is held on the holding region by the fixing member.

In the sample inspection method and sample inspection apparatus according to yet another embodiment of the present invention, during inspection of the sample, information about the film irradiated with the primary beam or the dose of the primary beam impinging on the film is monitored. Based on the result of the monitoring, the degree of irradiation damage to the film can be detected.

Consequently, when the damage to the film has increased to a considerable degree, destruction of the film due to the pressure difference can be prevented by stopping the beam irradiation of the film. This assures that the inside of the apparatus is prevented from being contaminated.

Furthermore, according to the present invention, a sample holder which is simple in structure and can be fabricated at low cost can be offered.

Other objects and features of the invention will appear in the course of the description thereof, which follows.

BRIEF DESCRIPTION OF THE DRAWINGS

FIG. 1 is a schematic cross section of a sample holder according to one embodiment of the present invention;

FIGS. 2A and 2B show perspective views of the sample holder shown in FIG. 1, showing the structure of the holder;

FIG. 3 is a schematic diagram of a sample inspection apparatus according to the first embodiment of the present invention;

DESCRIPTION OF THE PREFERRED EMBODIMENTS

First Embodiment

Figure 4:
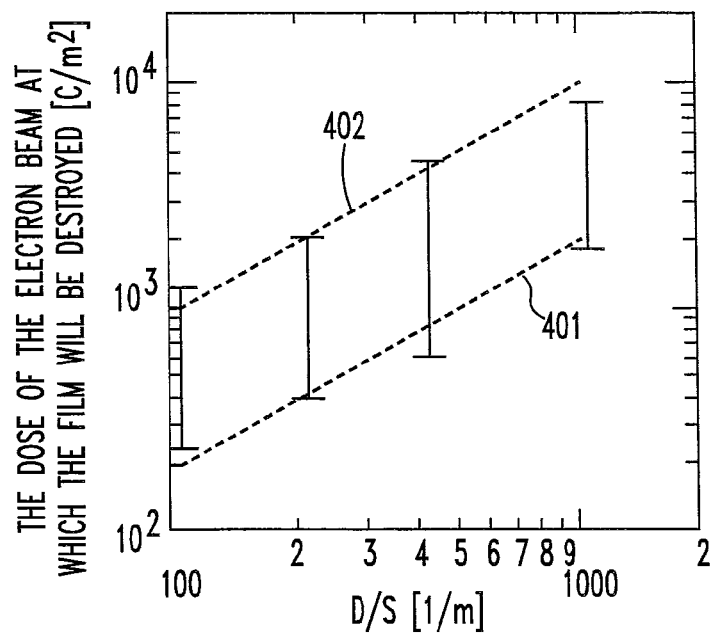
FIG. 4 is a graph showing the dose of an electron beam at which a film is destroyed.

FIG. 1 is a schematic cross section of a sample holder 1 for use in the present invention. The holder 1 is composed of a sample-holding member 2 and a base plate 3 which are bonded together with adhesive (not shown). The base plate 3 is made of silicon.

The sample-holding member 2 has a fixing member 5 and a sample-holding film 4. The fixing member 5 is provided with an opening 7 for forming a sample-holding space 6. The film 4 is coated on one surface of the fixing member 5 including the opening 7. A sample 520 is held in the sample-holding space 6. The film 4 is made of silicon nitride.

The sample-holding member 2 constructed in this way is shown in the perspective views of FIGS. 2A and 2B. In FIG. 2A, the sample-holding member 2 is in a state in which the other surface of the fixing member 5 forming the sample-holding member 2 faces upward. In FIG. 2B, the sample-holding member 2 has been rotated in reverse through 180° from the state shown in FIG. 2A. That is, one surface of the fixing member 5 on which the film 4 is coated faces upward.

As shown in FIG. 2A, the opening 7 is formed by wet etching around the center of the fixing member 5 on which the film 4 is coated. In this process of wet etching, only the silicon forming the fixing member 5 is etched away near the center of the fixing member 5, thus forming the opening 7. Within this opening 7, a part (sample-holding surface) 4a of the film 4 is exposed to an atmosphere.

The thickness of the film 4 is about 100 nm. The dimensions of the opening 7 are 0.5 mm×0.5 mm, for example. The opening 7 corresponds to a primary beam-irradiated region 7a through which an incoming primary beam is transmitted.

Under the condition shown in FIG. 2A, the sample 520 containing moisture is supplied into the opening 7 formed in the fixing member 5 excluding the sample-holding space 6 that is the inside space of the opening 7. Then, the base plate 3 is adhesively bonded to the other surface of the faxing member 5. Thus, the sample holder 1 is fabricated. Also, the sample 520 is held in the sample-holding space 6 formed by the opening 7. The pressure on the sample 520 held in the sample-holding space 6 is 1 atm.

The sample-holding member 2 having the sample-holding space 6 (opening 7) in which the sample is held is rotated in reverse through 180° from the state shown in FIG. 2A to the state shown in FIG. 2B. The above-cited FIG. 1 represents a cross section through a given portion of the sample-holding member 2 (FIG. 2B) to which the base plate 3 is adhesively bonded.

The sample holder 1 fabricated in this way is placed in the vacuum chamber 505 of the SEM 509 as shown in FIG. 3. The sample 520 is held in the sample-holding space 6 of the holder 1. FIG. 3 is a schematic diagram of the sample inspection apparatus according to the first embodiment of the present invention. The scanning electron microscope (SEM) 509 has the vacuum chamber 505, an electron optical column 501 mounted in the vacuum chamber 505, and pumps 506, 508 for evacuating the insides of the vacuum chamber 505 and of the electron optical column 501.

The present sample inspection apparatus includes an image-forming device, a display device, and a controller (none of which are shown), as well as the SEM 509. During irradiation by the electron beam 507, the pressure inside the electron optical column 501 is set to $10^{-4}$ to $10^{-5}$ Pa. The pressure inside the vacuum chamber 505 is set to $10^{-3}$ to $10^{-4}$ Pa.

The electron optical column 501 has an electron gun 502 acting as an electron source, condenser lenses 503 for focusing the electron beam (e.g., a beam of charged particles) 507 emitted from the electron gun 502 and directing the beam at the sample 520 held in the sample holder 1 within the vacuum chamber 505, a deflector (not shown) for scanning the electron beam 507, and a detector 504 located opposite to the sample holder 1 in the vacuum chamber 505. The detector 504 detects backscattered electrons emitted from the sample 520 held in the sample holder 1. The image-forming device forms an image (SEM image) of the sample based on the output signal from the detector 504 indicative of the detected electrons. The SEM 509 and image-forming device are appropriately controlled by the controller.

In the operation of the sample inspection apparatus constructed in this way, the sample holder 1 is first placed within the vacuum chamber 505 of the scanning electron microscope (SEM) 509. Then, the electron beam 507 is directed at the sample 520 via the film 4 on the sample holder 1. At this time, the film 4 is also irradiated with the beam 507.

During the irradiation, the probe current of the electron beam 507 is set to I A. A region on the film 4 scanned by the beam 507 is L m×M m. The time in which the region is scanned once by the beam 507 is T seconds. Let N be the number of times that the region is scanned with the beam 507. The dose of the electron beam 507 per unit area on the film 4 is given by $$(I \cdot T \cdot N)/(L \cdot M)$$

Assuming that I=500 pA, L=19 μm, M=25 μm, and T=80 s, we made an experiment using N as a parameter. It has been found that when N was 5 to 10, the film 4 was destroyed after it was damaged by the electron beam 507. At this time, the dose of the electron beam 507 was $4 \times 10^2$ C/m$^2$ to $8 \times 10^2$ C/m$^2$ in cases where N=5 to 10.

Similar experiments were performed under varied conditions. It has been found that the dose of the electron beam 507 at which the film 4 was destroyed was $4 \times 10^2$ C/m$^2$ to $2 \times 10^3$ C/m$^2$.

Let D [m] be the thickness of the film 4. Let S [m$^2$] be the area of the portion of the film 4 (i.e., the area of the region 7a irradiated with the primary beam) exposed through the opening 7. The dependence of film destruction on these amounts was also examined experimentally. It has been found that the dose of the electron beam 507 at which the film 4 is destroyed is in proportion to the film thickness D as shown in FIG. 4 and in inverse proportion to the area S. That is, it has been confirmed that the dose measured in C/m$^2$ of the electron beam 507 at which the film is destroyed is 2·D/S [1/m] (lower limit 401 in FIG. 4) to 10·D/S [1/m] (upper limit 402 in FIG. 4).

Therefore, destruction of the film 4 due to irradiation by the electron beam 507 is associated with the dose of the beam 507 impinging on the film 4. Consequently, in order to prevent destruction of the film 4, it is necessary that the dose of the electron beam 507 impinging on the film 4 be recorded and monitored and that the dose be controlled in such a way that the accumulated dose of the electron beam 507 does not exceed a reference value of electron beam dose at which the film 4 will be destroyed. For this purpose, the controller monitors whether or not the dose of the beam 507 impinging on the film 4 has reached the reference value as described later. Based on the results of the monitoring, the results of the monitoring are displayed, a warning is issued, or irradiation of the film 4 by the electron beam 507 is stopped. The monitoring is to check whether the monitored subject (in the present embodiment, the dose (accumulated dose) of the electron beam 507) has reached the given reference value.

Second Embodiment

Figure 5:
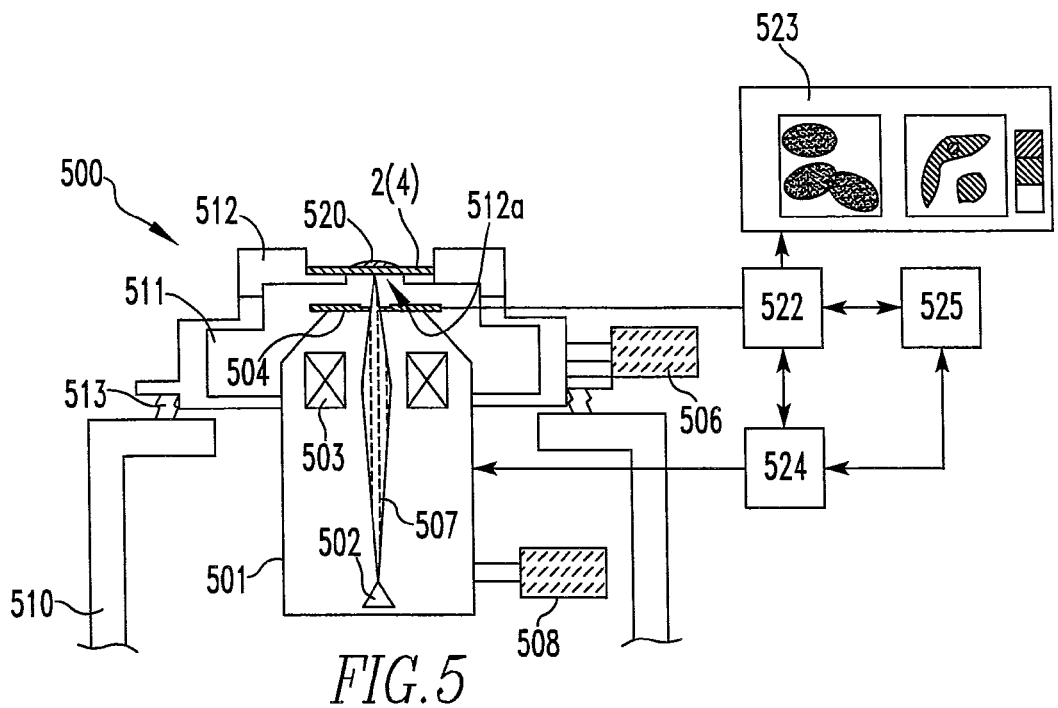
FIG. 5 is a schematic diagram of a sample inspection apparatus according to a second embodiment of the present invention.

FIG. 5 is a schematic diagram of a sample inspection apparatus according to the second embodiment of the present invention. In the present apparatus, an electron optical column that is mounted in a normal SEM is inverted. Furthermore, in the present apparatus, the sample 520 is placed in an open space located above the film 4 of the sample-holding member 2.

The sample-holding member 2 is identical in structure with the structure already described in the first embodiment in connection with FIG. 2A. Any surface of the film 4 formed on the sample-holding member 2 may be used as a top surface on which the sample is placed. However, the sample 520 needs to be placed on the region 7a of the film 4 irradiated with the primary beam. The surface (hereinafter may be referred to as the second surface) of the film 4 facing away from the surface on which the sample is placed is exposed to the ambient inside the vacuum chamber 511. Consequently, the second surface of the film 4 is exposed to the inside ambient.

Figure 6:
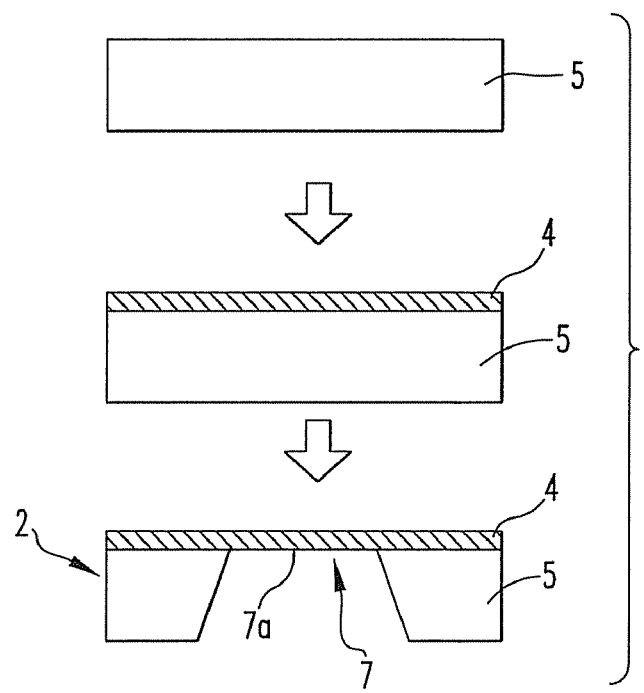
FIG. 6 illustrates a method of fabricating a sample holder according to the present invention.

A method of fabricating the sample-holding member 2 is described by referring to FIG. 6. The film 4 is formed from silicon nitride on one surface (in the figure, top surface) of the fixing member made of silicon. A beam of charged particles, such as an electron beam, is transmitted through the film 4.

Then, a central portion (corresponding to the region holding the sample) of the other surface (in the figure, the lower surface) of the fixing member 5 is etched away selectively such that the film 4 is left behind. In consequence, the opening 7 whose one side is coated with the film 4 is formed. A part of the film that is the sample-holding surface is exposed within the opening 7. This part of the film 4 becomes the region 7a of the film 4 irradiated with the primary beam. As a result, the sample-holding member 2 having the film 4 is created.

The thickness of the film 4 is set to a range from 10 to 1,000 nm. The film 4 transmits an electron beam but does not transmit gas or liquid. As described later, the electron beam 507 acting as a primary beam is directed at the sample 520 via the film 4. A secondary signal, such as backscattered electrons, emitted from the sample 520 in response to the irradiation is detected. In this way, the sample is inspected.

If the thickness of the film 4 is reduced, the electron beam 507 is scattered less within the film 4 and so the resolution is improved during the sample inspection. However, the rigidity decreases and the film becomes more susceptible to damage. Meanwhile, if the thickness of the film 4 is increased, the electron beam 507 is scattered more within the film 4 and so the resolution is deteriorated during the sample inspection. However, the rigidity increases and the film becomes less susceptible to damage. Therefore, a desirable range of thickness of the film 4 is from 20 to 200 nm.

Polymer, polyethylene, polyimide, polypropylene, carbon, silicon oxide, or boron oxide can be used as the material of the film 4, as well as silicon nitride. Where any one of these materials is used, the preferable range of thickness of the film 4 is from 10 to 1,000 nm. More preferably, the range is from 20 to 200 nm.

Referring to FIG. 5, the vacuum chamber 511 is placed over a pedestal 510 via a vibration-proofing device 513. A sample holder placement portion 512 is mounted on top of the vacuum chamber 511 and provided with a hole 512a permitting passage of the electron beam 507 emitted from the electron gun 502 acting as an electron source.

The sample-holding member 2 is placed over the sample holder placement portion 512 via an O-ring (not shown). Consequently, the sample-holding member 2 is supported such that it can be removably inserted into the vacuum chamber 511.

The O-ring is made of a resilient material and has flexibility. Therefore, the sample-holding member 2 has some degree of freedom of motion on the sample holder placement portion 512. That is, when an external horizontal force is applied to the sample-holding member 2, the O-ring is flexed appropriately. Concomitantly, the sample-holding member 2 can move a distance of 1 mm in the horizontal direction.

The electron optical column 501 is connected with the vacuum chamber 511. The electron gun 502 is placed on the column 501. The electron beam 507 acting as a primary beam is emitted from the gun 502 toward the sample 520 placed on the sample-holding member 2. The emitted beam 507 is accelerated by a given accelerating voltage.

The electron beam 507 is focused sharply by the condenser lenses (objective lens) 503. The focused beam 507 is transmitted through the region 7a of the film 4 to be irradiated with the primary beam, the film 4 being coated on the sample-holding member 2. As a result, the beam is made to hit the sample 520 via the film 4. At this time, the beam 507 is deflected by deflection apparatus (not shown) mounted in the electron optical column 501. Consequently, the electron beam 507 scans the sample 520.

Backscattered electrons are produced from the sample 520 irradiated with the electron beam 507. The electrons penetrate through the film 4 and are detected by the detector 504 mounted at the front end of the electron optical column 501.

When the electron beam 507 is being emitted from the electron gun 502, the inside spaces of the electron optical column 501 and the vacuum chamber 511 are evacuated by pumps 508 and 506 down to given levels of vacuum. At this time, the pressure inside the electron optical column 501 is set to $10^{-4}$ to $10^{-5}$ Pa. The pressure inside the vacuum chamber 511 is set to $10^{-3}$ to $10^{-4}$ Pa.

The output signal from the detector 504 indicating the detected backscattered electrons is fed to an image-forming device 522 located outside the vacuum chamber 511. The image-forming device 522 creates image data based on the detector output signal. The created image data becomes image data corresponding to an SEM image.

The image data is sent to a display device 523. The display device 523 displays an image based on the incoming image data. The displayed image is an SEM image.

The image data created by the image-forming device 522 is sent to the computer 525 as the need arises. The computer 525 performs given image processing on the image data. The image processing performed at this time is noise reduction, calculation of the area of the inspected object within the sample 520, identification of the shape, or extraction of the contour, for example.

The body 500 of the inspection apparatus having the electron optical column 501 and vacuum chamber 511, the image-forming device 522, and the computer 525 are controlled by a control portion 524. The control portion 524 can measure the beam current of the electron beam 507, detect secondary electrons emitted from the sample 520 during beam irradiation, or measure the absorption current.

When the sample-holding member 2 is placed on the sample holder placement portion 512 of the body 500 of the inspection apparatus, the insides of the vacuum chamber 511 and electron optical column 501 are at atmospheric pressure. After placing the sample-holding member 2 on the sample holder placement portion 512, the insides of the vacuum chamber 511 and electron optical column 501 are evacuated using the pumps 506 and 508. During the evacuation, in order to prevent damage to the film 4 (especially, the region 7a of the film 4 irradiated with the primary beam) due to a rapid variation from the atmospheric pressure, a needle valve (not shown) may be used to slow down the pumping process. In particular, the pumpdown is conducted for 1 to 100 seconds from 1 atm. (about 100 kPa) to ½ to ¹⁄₁₀ atm. (50 to 10 kPa). Then, pumpdown is performed down to the above-described pressure.

After checking that the film 4 of the sample-holding member 2 placed on the sample holder placement portion 512 is not destroyed by the above-described pumpdown sequence, the sample 520 is supplied to the top surface of the film 4 that is exposed to the atmosphere. As a result, the sample 520 is placed on the top surface of the film 4 of the sample-holding member 2. The sample 520 contains liquids, such as phosphate buffers and distilled water. The liquids contain an object to be inspected, such as red blood cells. The inspected subject precipitates in the liquids and settles down in contact with the top surface of the film 4.

In this embodiment, the top surface of the film 4 is exposed to the atmospheric-pressure ambient. In a case where it is necessary to prevent only evaporation of the moisture of the liquids, the top surface side of the film 4 may be pumped down to the ambient of water vapor pressure. This can reduce the pressure difference between the ambient on the top surface side of the film 4 and the ambient of the lower surface side (i.e., the ambient inside the vacuum chamber 511). Consequently, the probability that the film 4 is destroyed can be reduced.

After placing the sample 520 on the film 4 of the sample-holding member 2, the electron beam 507 is emitted from the electron gun 502, and the amount of beam current of the electron beam 507 is measured. For this measurement, a Faraday cup (not shown) is used. Instead of use of the Faraday cup, absorption current into the sample 520 may be measured.

The electron beam 507 whose beam current has been measured in this way is made to hit the sample 520 via the region 7a of the film 4 irradiated with the primary beam. At this time, the beam 507 is deflected by the deflection apparatus (not shown) and scans the sample 520.

Backscattered electrons produced from the sample 520 in response to the irradiation by the electron beam 507 are transmitted through the irradiated region 7a of the film 4 and reach the inside of the vacuum chamber 511, where the electrons are detected by the detector 504. The output signal from the detector 504 is fed to the image-forming device 522. The image-forming device 522 creates image data based on the output signal from the detector. The image data is sent to the display device 523, where an SEM image is displayed.

In the present embodiment, the dose of the electron beam 507 at which the film 4 is destroyed is set to $4 \times 10^2$ C/m² to $2 \times 10^3$ C·m², in the same way as in the first embodiment. Furthermore, in the same way as in the first embodiment, with respect to the dependence of film destruction on the thickness D [m] of the film 4 and on the area S [m²] of the portion (region 7a irradiated with the primary beam) of the film 4 exposed through the opening 7, the dose of the electron beam at which the film 4 is destroyed is in proportion to the thickness D of the film as shown in FIG. 4 and in inverse proportion to the area S. That is, the dose measured in C/m² of the beam 507 at which the film is destroyed is 2·D/S [1/m] (lower limit 401 in FIG. 4) to 10·D/S [1/m] (upper limit 402 in FIG. 4). A value set within this range is taken as a reference value of the dose of the electron beam.

Therefore, also in the example of the specimen inspection apparatus shown in FIG. 5, destruction of the film 4 due to irradiation by the electron beam 507 is associated with the dose of the beam 507 impinging on the film 4. Consequently, in order to prevent destruction of the film 4, it is necessary that the dose of the electron beam 507 impinging on the film 4 be recorded and monitored and that the dose be controlled in such a way that the accumulated dose of the electron beam 507 does not far exceed the reference value at which the film 4 will be destroyed. The monitoring is to check whether the monitored subject (in the present embodiment, the dose (accumulated dose) of the electron beam 507) has reached the given reference value.

Figure 7:
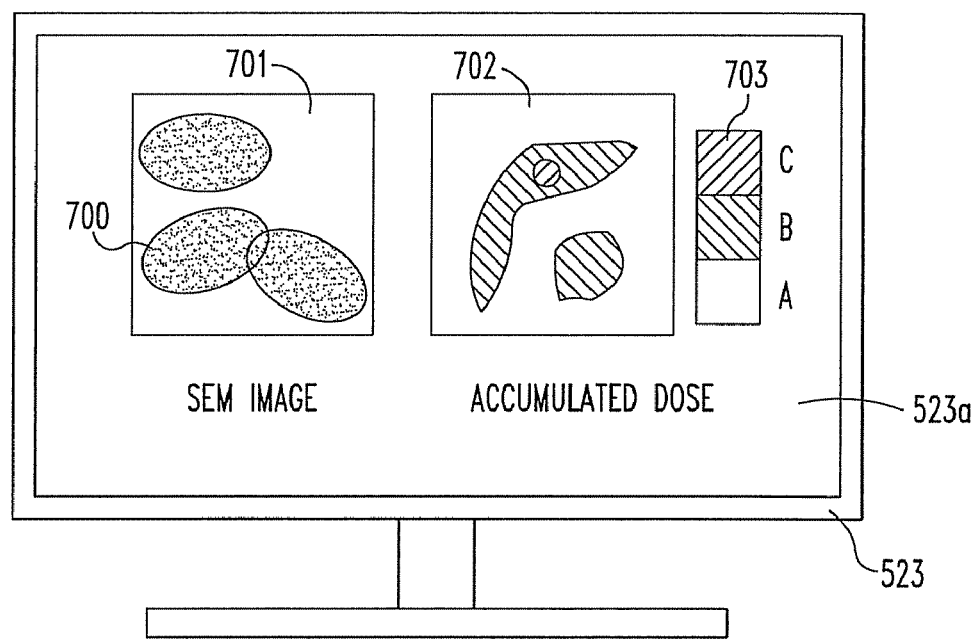
FIG. 7 schematically illustrates an example of a method of displaying an SEM image.

An example of display of an SEM image in the present embodiment where such control is provided is shown in FIG. 7. A display device 523 is a liquid crystal display and has a display screen 523a. In FIG. 7, an SEM image display region (window) 701 is present in the left portion within the display screen 523a. An SEM image of red blood cells 700 contained in the sample 520 is being displayed.

At the same time, the dose of the electron beam 507 impinging on the primary beam-irradiated region 7a of the film 4 coated on the sample-holding member 2 is recorded by the control portion 524. The result, i.e., the accumulated dose, is displayed on a dose display region (window) 702 of the right part within the display screen 523a, using contour lines. The range displayed in the dose display region 702 corresponds to the region 7a of the film irradiated with the primary beam. Consequently, the monitored subject (i.e., the dose of the electron beam 507) is monitored as an in-plane distribution across the film 4 and displayed.

The values of the dose of the electron beam 507 are represented by scale bars 703. The whole range of the values of the dose is divided into three subranges A, B, and C. In the subrange A, dose values are far below the reference value. In the subrange B, dose values are close to the reference value but still below it. In the subrange C, dose values are in excess of the reference value. Use of the scale bars is not limited to this method of dividing dose values into subranges as described above. For example, the scale bars may be used to indicate the numerical values indicating the accumulated dose or indexes indicating it.

If the time taken to observe and inspect the sample is prolonged, and if the beam irradiation time and dose are concomitantly increased, the above-described subrange C is produced in addition to the subranges A and B. The result is displayed in the dose display region 702. In consequence, the operator who manipulates the sample inspection apparatus can prevent the position in the primary beam-irradiated region 7a of the film 4 falling in the subrange C from being irradiated with the electron beam 507. As a result, the accumulated dose of the electron beam 507 can be prevented from far exceeding the reference value.

Figure 8:
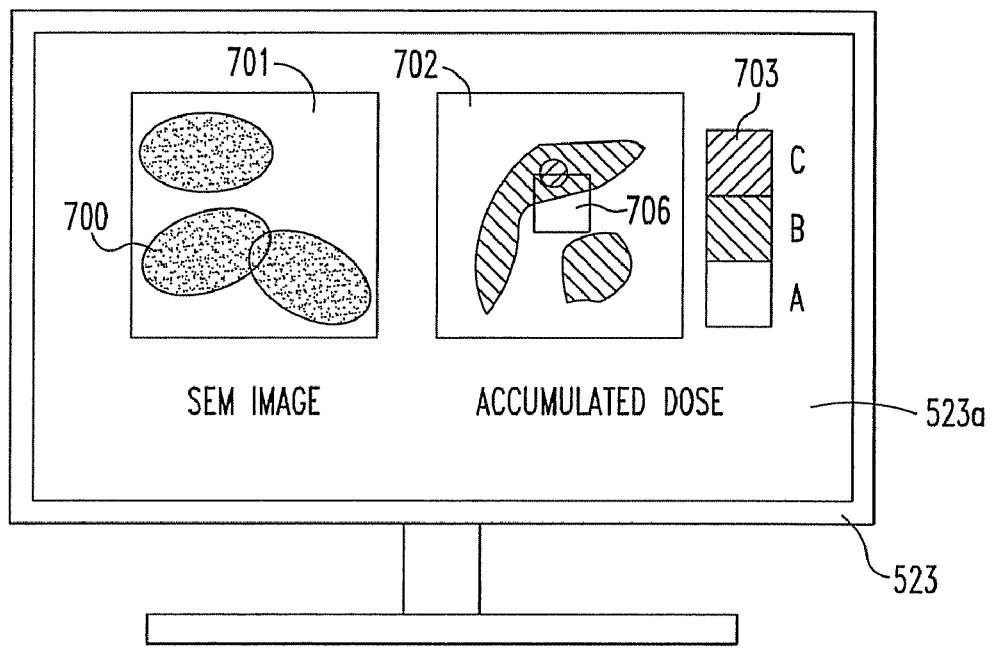
FIG. 8 schematically illustrates another example of a method of displaying an SEM image.

Another example of display is shown in FIG. 8. In this example, an observation region display frame 706 corresponding to the SEM image display region 701 is superimposed on the dose display region 702 within the display screen 523a of the display device 523. This superimposed display permits the operator to instantly recognize the dose of the electron beam 507 within the observation region display frame 706 corresponding to the SEM image. Unwanted impingement of the beam 507 on the region is prevented. This assures prevention of destruction of the film 4.

Figure 9:
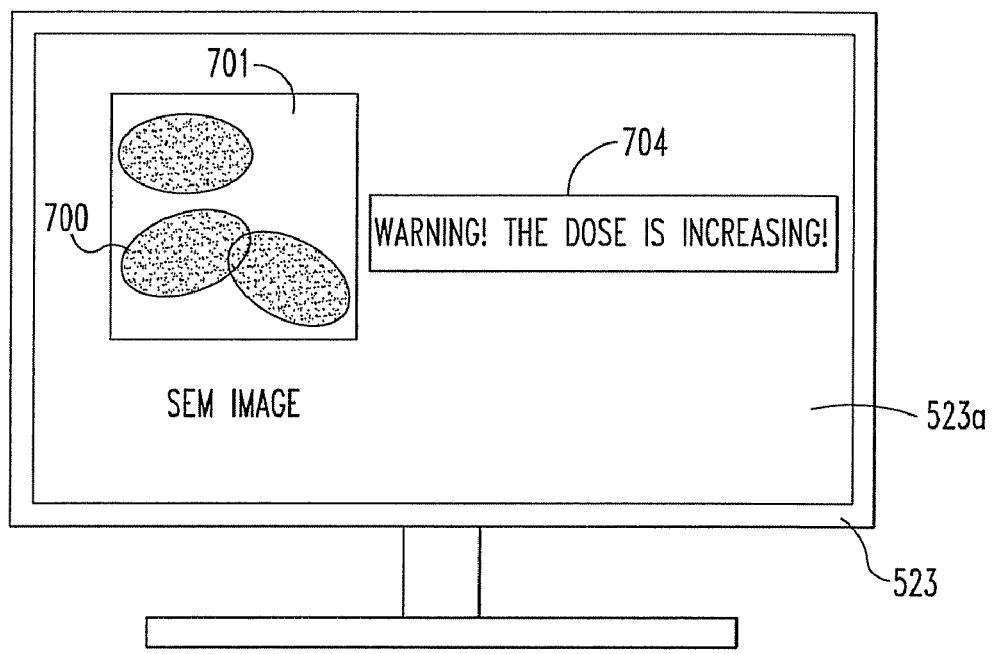
FIG. 9 schematically illustrates a further example of a method of displaying an SEM image.

A further example of display is shown in FIG. 9. In this example, an SEM image is displayed in the SEM image display region 701 within the display screen 523a of the display device 523. A warning 704 is displayed within the display screen 523a when the dose of the electron beam 507 impinging on the primary beam-irradiated region 7a of the film 4 exceeds the reference value. Consequently, a warning can be issued to the operator. When the warning 704 is displayed, the operator can recognize destruction of the film 4 to be imminent and stop the irradiation by the beam 507 before the film 4 is destroyed.

Figure 10:
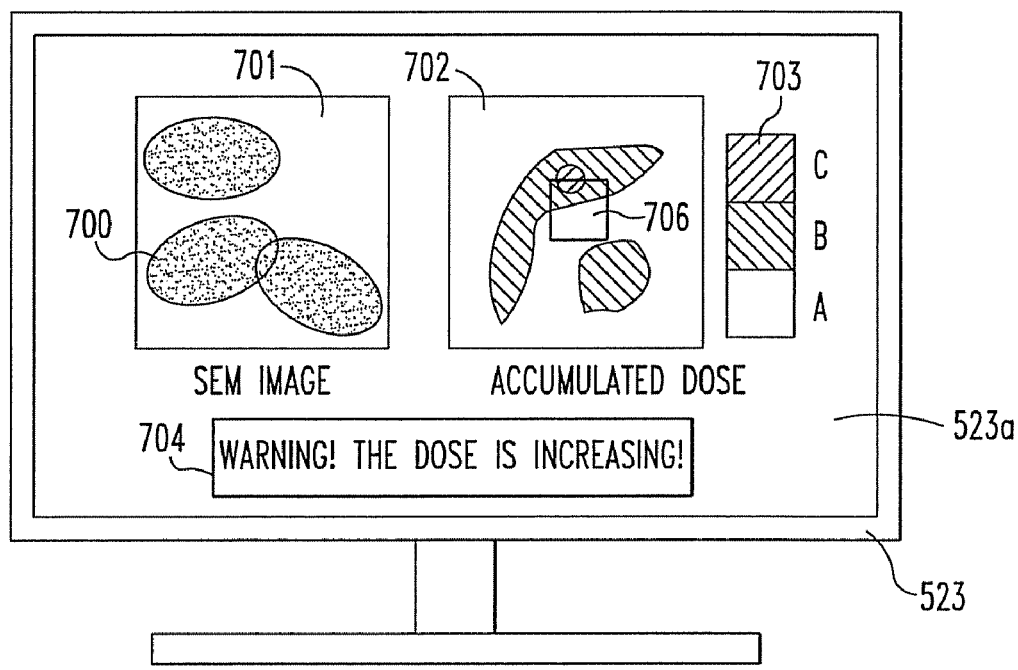
FIG. 10 schematically illustrates yet another example of a method of displaying an SEM image.

Still another example of display is shown in FIG. 10. In this example, an SEM image display region 701 and a dose display region 702 are established within the display screen 523a of the display device 523. Scale bars 703 are displayed. When the dose of the electron beam 507 impinging on the primary beam-irradiated region 7a of the film 4 exceeds the reference value, a warning 704 is displayed within the display screen 523a. A warning similar to the foregoing warning can be issued to the operator. The operator can stop the irradiation by the beam 507 before destruction of the film 4 occurs. This example is especially effective in preventing destruction of the film 4, because the operator can check the dose of the beam and, at the same time, can check the warning.

Figure 11:
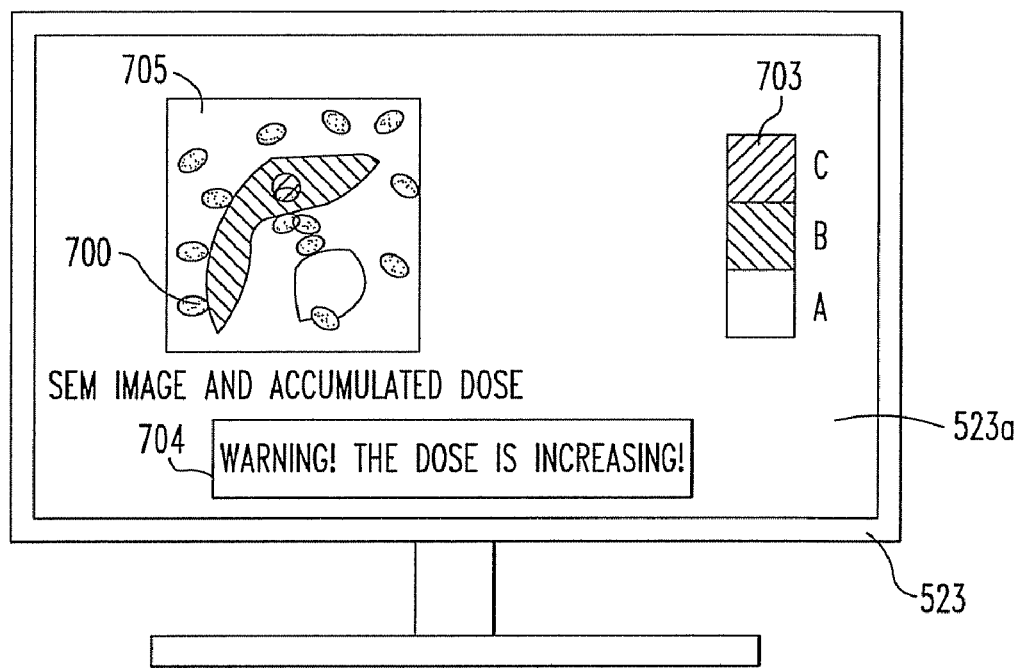
FIG. 11 schematically illustrates an additional example of a method of displaying an SEM image.

An additional example of display is shown in FIG. 11. In this example, a batch display region (window) 705 is established within the display screen 523a of the display device 523. Scale bars 703 are also displayed. In the batch display region 705, an SEM image and the dose 702 are displayed at the same time in a superimposed manner. Consequently, an in-plane distribution of the monitored subject (dose of the electron beam 507) across the film 4 is superimposed on an image created based on a secondary signal (backscattered electrons) produced from the sample 520 in response to the irradiation by the electron beam 507. In this case, the operator can grasp the interrelationship between the displayed SEM image and the displayed dose. The operator can check the dose of the beam 507 hitting the observed region at a glance and, therefore, this is effective in preventing destruction of the film 4.

The reference value of the dose measured in C/m² of the electron beam 507 is set within a range from 2·D/S [1/m] to 10·D/S [1/m] as mentioned previously. In this example, the thickness of the film 4 is set to D m. The area of the region 7a of the film 4 irradiated with the primary beam is set to S m².

With respect to the aforementioned irradiation by the electron beam 507, a process consisting of automatically cutting off the beam irradiation by blanking apparatus (not shown) when the dose of the beam 507 has reached a reference value may be carried out instead of or in addition to providing a display of the dose or issuing a warning as described previously. In this case, even if increases in the dose of the electron beam impinging on the film 4 due to a human error in manipulation cannot be prevented, the irradiation of the film 4 by the beam 507 can be stopped when the dose of the beam has reached the reference value. Therefore, destruction of the film 4 can be prevented with greater certainty.

The display of the dose (display of the result of monitoring), issuance of a warning, or stopping of the irradiation of the film 4 by the electron beam 507 can also be utilized for the sample inspection apparatus of the first embodiment (see FIG. 3) already described.

Additionally, the display of the dose (display of the result of monitoring), issuance of a warning, or stopping of the irradiation of the film 4 by the electron beam can also be utilized for a sample inspection apparatus consisting of a transmission electron microscope (TEM) or a scanning transmission electron microscope (STEM).

Figure 12:
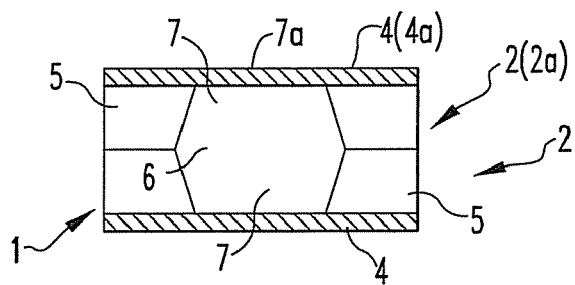
FIG. 12 is a cross section of a sample holder according to one embodiment of the present invention.

Referring to FIG. 12, the sample holder is fabricated by placing two sample-holding members 2 one atop another and bonding them together with adhesive. At this time, openings 7 formed in the fixing members 5 of the sample-holding members 2 are aligned to each other. Consequently, two films 4 are placed opposite to each other. A sample is held in a sample-holding space 6 formed between the films 4. The film 4a of one sample-holding member 2a of these two sample-holding members 2 has a region 7a irradiated with a primary beam.

An electron beam acting as the primary beam is directed at the sample placed within the sample-holding space 6 via the primary beam-irradiated region 7a of the film 4a coated on one sample-holding member 2. The electron beam (a secondary signal) transmitted through the sample passes through the film 4 coated on the other sample-holding member 2 and is detected by a detector mounted in the TEM or STEM. In this case, the dose of the electron beam impinging on the one film 4a having the primary beam-irradiated region 7a is monitored.

In each of the above examples, an electron beam is used as the primary beam. If the film 4 of the sample-holding member 2 shows sufficient resistance against irradiation by other charged-particle beam, such as an ion beam, as well as sufficient rigidity, other charged-particle beam can be used as the primary beam.

In each of the above examples, backscattered electrons or transmitted electrons are used as a secondary signal obtained when the sample is irradiated with the primary beam via the film 4. Besides, at least one kind of secondary electrons, absorption current into the sample, X-rays, and light (such as fluorescence) can be used.

In this way, in the sample inspection method according to the first or second embodiments, the sample 520 is irradiated with the primary beam 507, such as an electron beam, via the film 4. A secondary signal, such as backscattered electrons, produced from the sample 520 in response to the irradiation is detected to inspect the sample 520. In this sample inspection method, the dose of the primary beam 507 impinging on the film 4 is monitored.

Furthermore, a first sample inspection apparatus according to the first or second embodiment has: electron optical column 501 for directing the primary beam 507 at the sample 520 via the film 4; and signal detector 504 for detecting a secondary signal produced from the sample 520 in response to the irradiation by the primary beam 507. The apparatus includes the monitor 523 and control portion 524 for monitoring the irradiation of the film 4 by the primary beam 507.

Additionally, a second sample inspection apparatus according to the first or second embodiment has: a film 4 having a first surface on which a sample 520 is held; a vacuum chamber 511 for reducing the pressure of an ambient in contact with a second surface of the film 4; primary beam optical column 501 connected with the vacuum chamber 511 and irradiating the sample 520 with a primary beam 507 via the film 4; and signal detector 504 for detecting a secondary signal produced from the sample 520 in response to the irradiation by the primary beam 507. The apparatus includes monitoring control portion 524 for monitoring the dose of the primary beam 507 impinging on the film 4.

A third sample inspection apparatus according to the first or second embodiment has: two films 4 disposed opposite to each other such that a sample is held between mutually opposite surfaces of the films; a vacuum chamber 505 for reducing the pressure of an ambient in contact with the surfaces of the films 4 which face away from the mutually opposite surfaces; primary beam optical column 501 connected with the vacuum chamber 505 and irradiating the sample with a primary beam 507 via one of the films 4; and signal detector for detecting a secondary signal produced from the sample in response to the irradiation by the primary beam 507. The apparatus includes a monitoring control portion for monitoring the dose of the primary beam 507 impinging on the one film 4.

Third Embodiment

In the above-described first and second embodiments, the dose of the electron beam impinging on a film is recorded. The dose (accumulated dose) is prevented from far exceeding a preset reference value. In contrast, in the present embodiment, information about a film produced in response to electron beam irradiation is detected. Thus, a symptom of destruction of the film is captured. Consequently, destruction of the film is prevented.

That is, as the film is irradiated with the electron beam, the film is gradually damaged by the beam. Therefore, information based on a secondary signal derived from the film also varies gradually. Variations in the film are detected by detecting the secondary signal as information. A symptom of destruction of the film is captured by monitoring the secondary signal.

One example of information based on backscattered electrons produced from the film irradiated with an electron beam is information about the film, the latter information being obtained in response to the beam irradiation. In the present embodiment described below, an example in which backscattered electrons produced from a film are detected as a secondary signal is first described.

Figure 13:
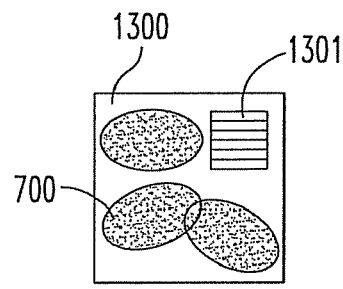
FIG. 13 illustrates the manner in which an SEM image is displayed in a third embodiment of the present invention.

FIG. 13 shows an SEM image 1300 obtained using the above-described sample inspection apparatus (see FIG. 5). An electron beam 507 is directed at a sample 520 (FIG. 5) via a film 4. Backscattered electrons emitted from the sample in response to the irradiation are detected by a detector 504. Based on the result of the detection, the SEM image 1300 is created and displayed.

The sample 520 contains red blood cells and is placed on the top surface of the film 4 forming a sample-holding member 2. The upper surface of the film 4 is exposed to the atmospheric-pressure ambient. The film 4 is made of silicon nitride and has a thickness of 100 nm. The displayed SEM image contains an image of the red blood cells 700 contained in the sample 520.

In the SEM image shown in FIG. 13, the average signal intensity (average brightness based on the result of detection of the backscattered electrons) in a region 1301 where the red blood cells did not exist was first recorded. The dependence on the number of shots (accumulated irradiation time) of the electron beam 507 was found. The average signal intensity derived by this region 1301 contains information based on backscattered electrons emitted from the film 4 excluding the inspected subject, i.e., the red blood cells 700.

Figure 14:
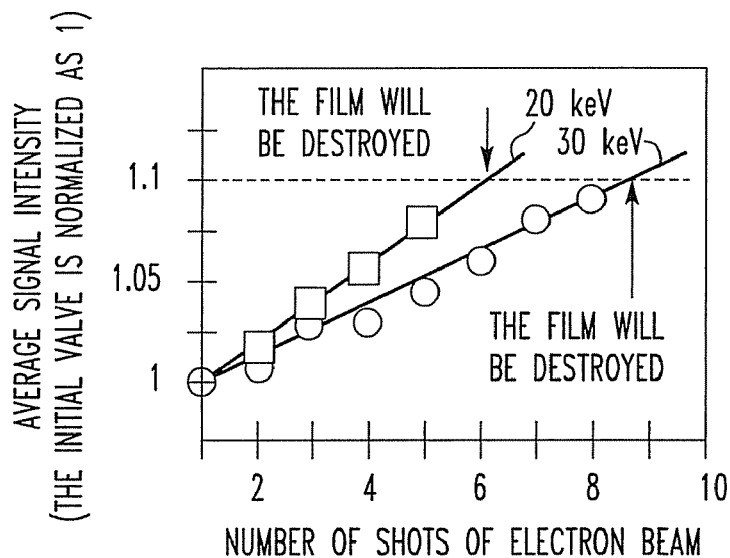
FIG. 14 is a graph in which the average signal intensity is plotted against the number of shots of an electron beam.

The found results are shown in FIG. 14. At this time, the irradiation energy of the electron beam 507 was 30 keV. The probe current was 500 pA. The area of the region (field of view) of the film 4 scanned by the electron beam 507 was 19 μm×25 μm. The time (shot time) taken to scan this region once by the beam 507 was 80 seconds.

The results are shown in FIG. 14. When the irradiation energy was 30 keV, the number of shots of the electron beam 507 increased. Also, the average signal intensity increased as indicated by ○ in the figure. It has been found that when the detected average signal intensity increased to a level that is 1.1 times as great as the first average signal intensity, the film 4 is destroyed. In the present experiment, the film 4 was destroyed when the number of shots was nine.

The irradiation energy of the electron beam 507 was then set to 20 keV, and similar experiments were performed. The results are indicated by □. It has been found that in the same way as in the foregoing, the film 4 was destroyed when the detected average signal intensity reached a level that was 1.1 times as great as the first average signal intensity. In the present experiment, the film 4 was destroyed when the number of shots was six.

As the irradiation energy (accelerating voltage) of the electron beam is reduced, the film is destroyed with a less number of shots of electron beam. The reason for this can be considered as follows. When the accelerating voltage of the electron beam is decreased, the scattering cross section due to the electron beam within the film increases, and the molecules constituting the film are more affected.

Accordingly, such experiments are previously performed. A value that is 1.1 times as great as the initial value obtained when irradiation by the electron beam 507 is started is taken as a reference value for the average signal intensity derived by detecting backscattered electrons. During sample inspection, the initial value of the average signal intensity produced by backscattered electrons emitted from the film 4 in response to the beam irradiation is recorded. When the sample inspection is being carried out, the control portion 524 monitors whether or not the average signal intensity has reached the reference value that is 1.1 times as great as the initial value.

The detector 504 produces a detection signal by detecting backscattered electrons. The control portion 524 finds the average signal intensity of the detection signal representing a region located outside the contour of the image of the inspected subject (in the above example, the red blood cells 700) within the sample 520, and monitors the average signal intensity. The detection signal representing the region does not contain information about the inspected subject but mainly contains information about the film 4 itself. Extraction of the contour of the image of the inspected subject is performed by the computer 525. In this case, the detector 504 acts also as means for detecting information about the film 4 (information based on the backscattered electrons) in response to the irradiation by the electron beam 507.

The control portion 524 monitors the average signal intensity. When the average signal intensity has reached the reference value, the control portion performs at least one of display of the results of the monitoring, issuance of a warning, and cutoff of the electron beam 507 in the same way as in the second embodiment. Consequently, destruction of the film 4 coated on the sample-holding member 2 can be prevented. Instead of making comparisons against the reference value, the amount of variation of the information (i.e., the amount of variation from the initial value) may be monitored. The monitoring is to check whether the monitored subject (in the present embodiment, information about the film 4 or an amount of variation of the information) has reached the given reference value.

In the above example, the average signal intensity of the detection signal indicative of backscattered electrons emitted from the film 4 is used as the information about the film 4. The information is not limited to this signal intensity. For example, secondary electrons produced from the film 4 or an absorption current produced in it in response to irradiation by the electron beam 507 may be detected, and the average signal intensity of the produced detection signal may be monitored by the control portion 524. In this case, the information detector for detecting information (information based on the secondary electrons or absorption current) about the film 4 in response to the irradiation by the electron beam 507 is a secondary electron detector or an absorption current detector (not shown).

The examples given in the third embodiment can be utilized when a sample is inspected using the sample inspection apparatus and sample holder described in both first and second embodiments.

In this way, the method of inspecting a sample in accordance with the third embodiment is carried out by irradiating a sample 520 with a primary beam (such as an electron beam) via the film 4 and detecting a secondary signal (such as backscattered electrons) produced from the sample 520 in response to the irradiation. Thus, the sample 520 is inspected. In this method, information (i.e., information based on backscattered electrons, secondary electrons, absorption current, or the like) about the film 4 obtained in response to the irradiation by the electron beam 507 is detected. The detected information about the film 4 is monitored.

A first sample inspection apparatus according to the third embodiment has: a primary beam optical column 501 for irradiating a sample 520 with a primary beam 507 via a film 4; and signal detector 504 for detecting a secondary signal produced from the sample 520 in response to the irradiation by the primary beam 507. The sample inspection apparatus includes: information detector 504 for detecting information about the film 4 obtained in response to the irradiation by the primary beam 507; and monitoring control portion 524 for monitoring the detected information about the film 4.

A second sample inspection apparatus according to the third embodiment has: a film 4 having a first surface on which a sample 520 is held; a vacuum chamber 511 for reducing the pressure of an ambient in contact with a second surface of the film 4; irradiation beam electron optical column 501 connected with the vacuum chamber 511 and irradiating the sample 520 with a primary beam 507 via the film 4; and signal detector 504 for detecting a secondary signal produced from the sample 520 in response to the irradiation by the primary beam 507. The sample inspection apparatus includes: information detector for detecting information about the film 4 obtained in response to the irradiation by the primary beam 507; and monitoring control portion 524 for monitoring the detected information about the film 4.

A third sample inspection apparatus according to the third embodiment has: two films 4 disposed opposite to each other such that a sample is held between mutually opposite surfaces of the films; a vacuum chamber 505 for reducing the pressure of an ambient in contact with the surfaces of the film 4 which faces away from the mutually opposite surfaces; an irradiation beam electron optical column 501 connected with the vacuum chamber 505 and irradiating the sample with a primary beam 507 via one of the two films 4; and signal detector for detecting a secondary signal produced from the sample in response to the irradiation by the primary beam. The sample inspection apparatus includes: information detector for detecting information about the one film 4 obtained in response to the irradiation by the primary beam 507; and monitoring control portion for monitoring the detected information about the film.

In all embodiments described above, a reference value is set for information about the film 4, an amount of variation of the information, or the dose of the primary beam 570. A control portion monitors whether or not the monitored subject has reached the reference value. In one feature of the present invention, the monitored subject (information about the film 4, an amount of variation of the information, or the dose of the primary beam 570) is monitored as an in-plane distribution across the film 4.

In another variation of the present invention, the in-plane distribution of the monitored subject is superimposed on an image created based on a secondary signal produced from the sample 520 in response to the irradiation by the primary beam.

In this way, in the present invention, either information about the film 4 irradiated with the primary beam 507 during sample inspection or the dose of the primary beam 507 impinging on the film 4 is monitored. Consequently, based on the results of the monitoring, the degree of damage to the film 4 due to the primary beam irradiation can be detected.

Therefore, when damage to the film 4 has increased, destruction of the film 4 due to a pressure difference can be prevented by stopping the irradiation of the film 4 by the primary beam 507. This assures prevention of contamination inside the apparatus.

In addition, the aforementioned sample holder is simple in structure and can be fabricated at low cost. Moreover, according to the above-described method of fabricating a sample holder, the sample holder can be fabricated efficiently and at low cost.

Having thus described my invention with the detail and particularity required by the Patent Laws, what is desired protected by Letters Patent is set forth in the following claims.

The invention claimed is:

1. A method of inspecting a sample by irradiating the sample with a primary beam via a film and detecting a secondary signal produced from the sample in response to the irradiation,
    wherein information about the film obtained in response to the irradiation is monitored, and/or a dose of the primary beam impinging on the film is monitored.

2. A method of inspecting a sample as set forth in claim 1, wherein said information about the film is information based on backscattered electrons, secondary electrons, or an absorption current produced from or in the film.

3. A method of inspecting a sample as set forth in any one of claims 1 and 2, wherein a reference value is set for said information about the film, an amount of variation in the information, or a dose of said primary beam, and wherein the monitored subject is monitored whether or not it has reached the reference value.

4. A method of inspecting a sample as set forth in claim 3, wherein said primary beam is an electron beam, and wherein the dose measured in $C/m^2$ of the primary beam is monitored to determine whether or not it has reached the reference value [$C/m^2$] set within a range of $2 \cdot D/S$ [1/m] to $10 \cdot D/S$ [1/m], where $D$ [m] is the thickness of the film and $S$ [$m^2$] is the area of a portion of the film irradiated with the primary beam.

5. A method of inspecting a sample as set forth in claim 1, wherein said information about the film, an amount of variation in the information, or a dose of said primary beam is monitored as an in-plane distribution across the film.

6. A method of inspecting a sample as set forth in claim 1, wherein at least one of display of the results of the monitoring, issuance of a warning, and cutoff of the irradiation of the film with the primary beam is performed.

7. A method of inspecting a sample as set forth in claim 1, wherein an in-plane distribution of information about the film, an amount of variation in the information, or a dose of the primary beam is superimposed on an image created based on the secondary signal produced from the sample.

8. A method of inspecting a sample as set forth in claim 1, wherein said primary beam is an electron beam, and wherein said secondary signal is at least one kind of backscattered electrons, secondary electrons, absorption current, X-rays, and light.

9. A sample inspection apparatus having a film having a first surface on which a sample is held, a vacuum chamber for reducing the pressure of an ambient in contact with a second surface of the film, irradiation means connected with the vacuum chamber and irradiating the sample with a primary beam via the film, and signal detection means for detecting a secondary signal produced from the sample in response to the irradiation,
    wherein said apparatus further includes monitoring means for monitoring information about the film obtained in response to the irradiation and/or monitoring means for monitoring a dose of the primary beam impinging on the film.

10. A sample inspection apparatus having two films disposed opposite to each other such that a sample is held between mutually opposite surfaces of the films, a vacuum chamber for reducing the pressure of an ambient in contact with surfaces of the films facing away from said mutually opposite surfaces, irradiation means connected with the vacuum chamber and irradiating the sample with a primary beam via one of the two films, and signal detection means for detecting a secondary signal produced from the sample in response to the irradiation,
    wherein said apparatus further includes monitoring means for monitoring information about the film obtained in response to the irradiation and/or monitoring means for monitoring a dose of the primary beam impinging on the film.

11. A sample inspection apparatus as set forth in any one of claims 9 and 10, wherein a reference value is set for a monitored subject that is information about the film, an amount of variation in the information, or the dose of the primary beam, and wherein said monitoring means monitors whether or not the monitored subject has reached the reference value.

12. A sample inspection apparatus as set forth in claim 11, wherein said primary beam is an electron beam, and wherein said monitoring means monitors to determine whether or not the dose measured in $C/m^2$ of the primary beam is monitored whether or not it has reached the reference value set within a range of $2 \cdot D/S$[1/m] to $10 \cdot D/S$ [1/m], where $D$ [m] is the thickness of the film and $S$ [$m^2$] is the area of a portion of the film irradiated with the primary beam.

13. A sample inspection apparatus as set forth in claim 9, wherein said monitoring means monitors said information about the film, an amount of variation in the information, or a dose of said primary beam as an in-plane distribution across the film.

14. A sample inspection apparatus as set forth in claim 9, further including at least one of means for displaying results of monitoring done by said monitoring means, means for issuing a warning based on the results of the monitoring, and means stopping the film from being irradiated with the primary beam based on the results of the monitoring.

15. A sample inspection apparatus as set forth in claim 9, further including means for superimposing an in-plane distribution of information about the film, an amount of variation in the information, or a dose of the primary beam onto an image created based on a secondary signal produced from the sample.

16. A sample inspection apparatus as set forth in claim 9, wherein said primary beam is an electron beam, and wherein said secondary signal is at least one kind of backscattered electrons, secondary electrons, absorption current, X-rays, and light.

17. A sample holder comprising:
   a film through which a charged-particle beam is transmitted, the film having a first surface on which a sample is placed in an open atmosphere, the sample holder permitting the sample to be irradiated with the charged-particle beam from a side of a second surface of the film via the film; and
   a fixing member mounted on the first surface of the film except for a sample-holding region of the first surface of the film, the fixing member holding the sample on the holding region.

18. A method of inspecting a sample comprising the steps of:
   preparing a sample holder comprising:
   a film through which a charged-particle beam is transmitted, the film having a first surface on which a sample is placed in an open atmosphere, the sample holder permitting the sample to be irradiated with the charged-particle beam from a side of a second surface of the film via the film; and
   a fixing member mounted on the first surface of the film except for a sample-holding region of the first surface of the film, the fixing member holding the sample on the holding region,
   placing the sample on said holding region of the sample holder;
   irradiating the sample with a charged-particle beam from a side of a second surface of the film forming the sample holder via the film; and
   detecting a secondary signal produced from the sample in response to the irradiation and obtaining information about the sample.

* * * * *